US008552071B1

(12) United States Patent
Daniel et al.

(10) Patent No.: US 8,552,071 B1
(45) Date of Patent: Oct. 8, 2013

(54) HYDROGELS ABSORBING AQUEOUS FLUIDS

(75) Inventors: Thomas Daniel, Waldsee (DE); Ulrich Riegel, Frankfurt (DE); Matthias Weismantel, Jossgrund (DE); Norbert Herfert, Altenstadt (DE); Friedrich Engelhardt, Frankfurt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 09/831,915

(22) PCT Filed: Nov. 18, 1999

(86) PCT No.: PCT/EP99/08850
§ 371 (c)(1),
(2), (4) Date: May 25, 2001

(87) PCT Pub. No.: WO00/31157
PCT Pub. Date: Jun. 2, 2000

(30) Foreign Application Priority Data

Nov. 26, 1998 (DE) ................................. 198 54 575

(51) Int. Cl.
A61L 15/60 (2006.01)
C08L 33/02 (2006.01)
C08F 20/04 (2006.01)
C08F 2/44 (2006.01)
C08K 3/34 (2006.01)
C08K 3/36 (2006.01)
A61F 13/53 (2006.01)
A61F 13/15 (2006.01)
A61F 13/49 (2006.01)
A61F 5/44 (2006.01)

(52) U.S. Cl.
USPC ........... 516/100; 524/492; 524/556; 524/609; 524/610; 524/650; 524/791; 524/916

(58) Field of Classification Search
USPC .......... 516/100; 524/430, 492, 556, 609, 610, 524/916, 650, 791
See application file for complete search history.

(56) References Cited

U.S. PATENT DOCUMENTS

| 2,411,899 | A | * | 12/1946 | Semegen | 525/330.6 |
|---|---|---|---|---|---|
| 4,286,082 | A | | 8/1981 | Tsubakimoto et al. | 526/240 |
| 4,350,775 | A | * | 9/1982 | Blount | 521/100 |
| 4,352,884 | A | * | 10/1982 | Nakashima et al. | 435/180 |
| 4,512,808 | A | * | 4/1985 | Pesch et al. | 524/5 |
| 4,535,098 | A | | 8/1985 | Evani et al. | 521/149 |
| 4,654,039 | A | * | 3/1987 | Brandt et al. | 604/368 |
| 4,666,983 | A | | 5/1987 | Tsubakimoto et al. | 525/119 |
| 4,707,290 | A | * | 11/1987 | Seiter et al. | 510/443 |
| 4,734,478 | A | | 3/1988 | Tsubakimoto et al. | 527/300 |
| 4,931,497 | A | | 6/1990 | Engelhardt et al. | 525/42 |
| 4,990,338 | A | | 2/1991 | Blank et al. | 525/279 |
| 5,011,892 | A | | 4/1991 | Engelhardt et al. | 525/404 |
| 5,032,628 | A | | 7/1991 | Choi et al. | 523/409 |
| 5,035,892 | A | | 7/1991 | Blank et al. | 424/443 |
| 5,053,135 | A | * | 10/1991 | Boschetti et al. | 210/635 |
| 5,055,501 | A | | 10/1991 | Moriya et al. | 523/409 |
| 5,066,745 | A | | 11/1991 | Engelhardt et al. | 526/240 |
| 5,075,371 | A | * | 12/1991 | Boschetti et al. | 524/791 |
| 5,140,076 | A | | 8/1992 | Hatsuda et al. | 525/375 |
| 5,409,771 | A | | 4/1995 | Dahmen et al. | 428/327 |
| 5,429,628 | A | * | 7/1995 | Trinh et al. | 604/359 |
| 5,712,316 | A | | 1/1998 | Dahmen et al. | 521/72 |
| 6,472,478 | B1 | * | 10/2002 | Funk et al. | 525/327.6 |
| 6,503,979 | B1 | * | 1/2003 | Funk et al. | 524/556 |
| 6,559,239 | B1 | * | 5/2003 | Riegel et al. | 525/329.7 |
| 6,565,768 | B1 | * | 5/2003 | Dentler et al. | 252/194 |
| 6,657,015 | B1 | * | 12/2003 | Riegel et al. | 525/329.9 |

FOREIGN PATENT DOCUMENTS

| CH | 185 779 | 11/1936 |
|---|---|---|
| DE | 33 14 019 | 1/1984 |
| DE | 35 23 617 | 1/1986 |
| DE | 37 37 196 | 5/1988 |
| DE | 40 20 780 | 8/1991 |
| DE | 44 18 818 | 1/1995 |
| DE | 195 43 366 | 5/1997 |
| DE | 198 07 504 A1 * | 8/1999 |
| EP | 0 205 674 | 12/1986 |
| EP | 0 227 666 | 7/1987 |
| EP | 0 316 792 | 5/1989 |
| EP | 0 317 106 | 5/1989 |
| EP | 0 341 951 | 11/1989 |
| EP | 0 343 427 | 11/1989 |
| EP | 0 349 240 | 1/1990 |
| EP | 0 400 283 | 12/1990 |
| EP | 0 450 922 | 10/1991 |
| EP | 0 450 923 | 10/1991 |

(Continued)

OTHER PUBLICATIONS

Japan Patent Office, Machine translation of JP 06-016822 on the internet at http://www19.ipdl.jpo.go.jp/PA1/cgi-bin/PA1INDEX (Jul. 2004).*

(Continued)

Primary Examiner — Daniel S Metzmaier
(74) Attorney, Agent, or Firm — Oblon, Spivak, McClelland, Maier & Neustadt, L.L.P.

(57) ABSTRACT

The invention relates to hydrogels capable of absorbing aqueous fluids, which hydrogels are produced by polymerization of olefinically unsaturated carboxylic acids or their derivatives. The hydrogels are characterized in that before, during or after the polymerization reaction and before drying a silicic acid alkali salt of the general formula (I) $M_2O \times nSiO_2$ is added to the polymerization reaction mixture. In said formula M is an alkali metal and n is a number between 0.5 and 4. The hydrogel obtained in this way is then dried at an elevated temperature. The invention also relates to a method for producing said hydrogels and to their use for absorbing aqueous fluids.

18 Claims, No Drawings

(56) References Cited

FOREIGN PATENT DOCUMENTS

| EP | 0 471 595 |   | 2/1992 |
|----|-----------|---|--------|
| EP | 0 629 411 |   | 12/1994 |
| EP | 0 640 330 |   | 3/1995 |
| JP | 06-016822 | * | 1/1994 |
| WO | WO 93/17066 |   | 9/1993 |
| WO | WO 97/46189 | * | 12/1997 |
| WO | WO 97/46195 | * | 12/1997 |

OTHER PUBLICATIONS

Derwent Abstract on East, week 199409, London: Derwent Publications Ltd., AN 1994-068615, Class A14, JP 06-016822 A, (Sekisui Plastics Co Ltd), abstract.*

Derwent Abstract on East, week 198148, London: Derwent Publications Ltd., AN 1981-88113D, JP 56-133028 A, (Nippon Shokubai Kogyo Co Ltd), abstract.*

"Modern Superabsorbent Polymer Technology", edited by Fredric L. Buchholz and Andrew T. Graham, Wiley-VCH, pp. 97-101, Nov. 1997.

F.L. Bucholz and A.T. Graham, Modern Superabsorbent Polymer Technology, pp. 6-7, Nov. 1997.

Ulmann's Encyclopedia of Industrial Chemistry, $6^{th}$ Edition, vol. 35, pp. 73-74.

Kirk-Othmer, Encyclopedia of Chemical Technology, $4^{th}$ Edition, vol. 8, pp. 108-109.

Ullmann's, Encyclopedia of Industrial Chemistry, $6^{th}$ Edition, Completely Revised Edition, vol. 32, pp. 411-413.

* cited by examiner

HYDROGELS ABSORBING AQUEOUS FLUIDS

The present invention relates to hydrogels prepared using silicates, a process for their preparation and their use for absorbing aqueous fluids.

The inventive hydrogels capable of absorbing aqueous fluids are water-insoluble carboxylate polymers which contain a polysilicate matrix and are capable of swelling and forming hydrogels to absorb aqueous fluids and body fluids, for example urine or blood, and to retain the absorbed fluid under a certain pressure.

To prepare polymers capable of forming hydrogels having a particularly high absorption capacity, a high gel strength and high absorbency under load, the addition polymer particles may be subjected to a subsequent surface treatment, postcrosslinking.

Postcrosslinking is preferably effected using compounds known as crosslinkers which contain two or more groups capable of forming covalent bonds with the carboxyl groups of the hydrophilic polymers, see EP-A-0 349 240.

Known crosslinkers are polyglycidyl ethers, haloepoxy compounds, polyols, polyamines or polyisocyanates. DE-A-3 314 019, EP-A-0 317 106 and DE-A-3 737 196 further mention polyfunctional aziridine compounds, alkyl di(tri) halides and oil-soluble polyepoxy compounds as crosslinkers.

According to DE-A-4 020 780 improved absorbency under load is obtained by surface crosslinking treatment of the polymer with from 0.1 to 5% by weight of alkylene carbonate.

The subsequent addition of finely divided amorphous silicas such as AERIL® or CAB-O-SIL® or bentonites atop the surface of powders or granules to finish absorbent polymers is likewise known. EP-A-0 450 923, EP-A-0 450 922, DE-A-3 523 617, U.S. Pat. No. 5,140,076 and U.S. Pat. No. 4,734,478 teach the addition of silica in the course of the process of surface postcrosslinking dry powders of absorbent polymers using carboxyl-reactive crosslinkers. U.S. Pat. No. 4,286,082 describes the use of mixtures of silica with absorbent polymers for use in hygiene articles. JP 65 133 028A and JP 61 017 542B describe blends of hydrophobic silica types with absorbent polymers. EP-A-0 341 951, U.S. Pat. No. 4,990,338 and U.S. Pat. No. 5,035,892 describe the use of silica in the production of antimicrobially finished absorbent polymers. U.S. Pat. No. 4,535,098 and EP-A-0 227 666 finally describe the addition of colloidal carrier substances based on silica to enhance the gel strength of absorbent polymers.

These "dry" blends, where the additives merely adhere to the surface of the polymer, however, modify the characteristic profile of the absorbent hydrogels, for example rendering them hydrophilic or hydrophobic, which primarily affects the absorption rate. In addition, the gel strength of the swollen particles is also increased in part, but it is a common feature of all these polymers that the permeability through swollen gel is unsatisfactory, regardless of the acquisition time.

It is an object of the present invention to provide novel hydrogels possessing in particular improved mechanical stability and enhanced permeability of the swollen gel particles. This object is to be achieved without any of the customary cross linkers.

We have found that this object is achieved, surprisingly, by the use of silicates which are added to the hydrogels before, during or after the polymerization reaction, but before the drying of the hydrogels.

The present invention accordingly provides hydrogels capable of absorbing aqueous fluids, prepared by polymerization of olefinically unsaturated carboxylic acids or derivatives thereof, wherefor the polymerization reaction mixture is admixed with an alkali metal silicate of the general formula I $$M_2O \times n SiO_2 \qquad (I),$$

where M is an alkali metal and n is generally from 0.5 to 4, before, during or after the polymerization reaction and before drying and the hydrogel thus obtained is then dried at elevated temperature.

The compounds of the formula I are preferably used in amounts of from 0.05 to 100%, particularly preferably from 1 to 70%, especially from 1 to 40%, specifically from 1 to 20%, by weight, reckoned on $SiO_2$ and based on the total monomer weight; that is, the use of 100% by weight of compounds of the formula I represents the use of equal weights of monomers and silicates. M is preferably sodium or potassium.

The preparation of these alkali metal silicates is common knowledge and is effected by reacting aqueous alkali with $SiO_2$ or by fusing quartz sand with alkali metal carbonates at high temperatures in a molar ratio of from 1:2 to 4:1. The cooled glassy melts are soluble in water and are therefore also known as "waterglasses".

The commercially available aqueous solutions of alkali metal silicates of the formula I are produced by dissolving the solid melts in superheated water under pressure.

The aqueous solutions of alkali metal silicates (waterglasses) give an alkaline reaction as a consequence of partial hydrolysis. As well as alkali metal and hydroxide ions, they also contain monosilicate ions, $HSiO_4^{3-}$, $H_2SiO_4^{2-}$ and $H_3SiO_4^-$ and also cyclic and three-dimensionally crosslinked polysilicate ions.

On acidification, aqueous alkali metal silicate solutions form spherical amorphous silicas, known as silica sols, which tend to form a gellike mass (silica hydrogels). It comprises a polycondensate of spherical silicas which is pervaded by numerous water-filled pores. Drying of the hydrogel at relatively high temperatures gives solid silica gels, specifically "silica aerogels".

Useful olefinically unsaturated carboxylic acids or derivatives thereof include in particular acrylic acid, methacrylic acid, crotonic acid, 2-acrylamido-2-methylpropanesulfonic acid and -phosphonic acid, vinylphosphonic acid, vinylphosphonic monoesters, salts thereof, acrylamide, N-vinylamides or mixtures thereof. Preference is given to acrylic acid and its salts.

The preparation and use of such polymers capable of hydrogel formation is described in numerous patent specifications such as EP-A-0 316 792, EP-A-0 400 283, EP-A-0 343 427, EP-A-0 205 674 and DE-A-4 418 818.

The polymerization is preferably carried out in a homogeneous phase, for example in an aqueous solution, as a gel polymerization.

The polymerization, as will be general knowledge, can be initiated by free radical formers, for example organic or inorganic peroxides and also azo compounds. Examples are benzoyl peroxide, tert-butyl hydroperoxide, cumene hydroperoxide, $(NH_4)_2S_2O_8$, $K_2S_2O_8$, $H_2S_2O_8$, $H_2O_2$ or azodiisobutyronitrile. Redox systems are also very useful as polymerization initiators.

The polymerization may finally also be initiated by means of high energy radiation.

Preferably, the acidic addition polymers are neutralized with mixtures of alkali metal silicates and alkali metal hydroxides, preferably in the form of the aqueous solutions, after the polymerization. It is likewise preferable to neutralize the acidic addition polymers with mixtures of alkali metal silicates and alkali metal carbonates.

The acidic addition polymers are preferably neutralized to a pH in the range from 3.5 to 9.0, especially 4.0-6.5.

The temperatures for the subsequent drying of the hydrogels are preferably in the range from 40° C. to 300° C., especially in the range from 120° C. to 220° C.

At a polymer pH of from 5.0 to 9.0, the gel permeability, measured as GLP, is preferably at least $25 \times 10^{-7}$ cm$^3$ sec/g, particularly preferably at least $45 \times 10^{-7}$ cm$^3$ sec/g, especially at least $60 \times 10^{-7}$ cm$^3$ sec/g.

At a polymer pH of less than 5.0, the gel permeability, measured as GLP, is in particular at least $4 \times 10^{-7}$ cm$^3$ sec/g, preferably at least $10 \times 10^{-7}$ cm$^3$ sec/g, particularly preferably at least $20 \times 10^{-7}$ cm$^3$ sec/g.

The hydrogels of the invention are very useful as absorbents for aqueous fluids, for example for absorbing aqueous solutions, dispersions and emulsions, especially for absorbing body fluids such as blood and urine, for producing articles for absorbing aqueous fluids and for producing absorbent hygiene articles.

Hydrogels of the invention which are based on acrylic acid are particularly useful as superabsorbent polymers (SAPs) for use in hygiene articles, for example diapers, tampons or sanitary napkins, for which they may be partly present as alkali metal or amine salt. Neutralization is effected according to the invention by addition of alkali metal silicates.

Postcrosslinking, especially in the surface, with mono-, bis- and polyoxazolidinones, with the cyclic ester of propanediol with silicic acid of the formula II

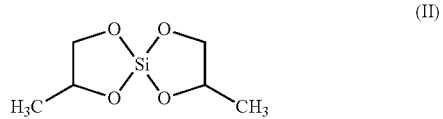

(II)

or with compounds which contain at least 2 carboxyl-reactive functional groups in the molecule, such as di-, tri- or polyepoxides, for example ethylene glycol diglycidyl ether or haloepoxy compounds or polyamine compounds and also polyhydric alcohols such as ethylene glycol, propylene glycol, trimethylolpropane, substantially improves performance with regard to absorbency under load.

The polymer of the invention has a harder, more crystalline character in the swollen state, which not only suppresses stickiness but also results in improved fluid transportation or drainage, especially under a restraining force.

The examples hereinbelow illustrate the preparation and properties of polymers according to the invention and the test methods for determining the properties of the hydrogels.

Test Methods

Centrifuge Retention Capacity (CRC):

This method determines the free swellability of the hydrogel in a teabag. $0.2000 \pm 0.0050$ g of dried hydrogel are welded into a teabag (format: 60 mm×60 mm, Dexter 1234T paper) and soaked for 30 minutes in a 0.9% by weight sodium chloride solution. The teabag is then centrifuged for 3 min in a commercially available spin dryer (1400 rpm, basket diameter 230 mm). The absorbed amount of liquid is determined by weighing the centrifuged teabag.

To allow for the absorption capacity of the teabag itself, the test is also carried out on a teabag without water-absorbent hydrogel, as a blank.

Retention CRC [g/g]=(final weight–blank value–starting weight)/starting weight where final weight is the wet weight of the swollen and centrifuged teabag plus contents starting weight is the dry sample weight and blank value is the wet weight of the empty teabag after centrifuging.

Absorbency Under Load:

$0.1600 \pm 0.0050$ g of dry hydrogel are uniformly distributed on the sieve base of a measuring cell. The measuring cell consists of a Plexiglas cylinder 33 mm in height and 25 mm in diameter, to which a 36 micron steel mesh has been adhered as base.

A covering plate is placed on top of the uniformly distributed hydrogel and loaded with an appropriate weight. The cell is placed in a Petri dish 10 mm in height and 100 mm in diameter, which contains 13 ml of 0.9% by weight sodium chloride solution. The hydrogel is allowed to absorb the salt solution for 60 min. The complete cell with the swollen gel is then removed from the Petri dish and after the weight has been removed the apparatus is reweighed.

Absorbency under load AUL is calculated as follows:

AUL [g/g]=($Wb-Wa$)/$Ws$ where

Wb is the mass of the apparatus+gel after swelling,

Wa is the mass of the apparatus+starting weight before swelling, and

Ws is the starting weight of dry hydrogel.

The apparatus consists of measuring cylinder+covering plate.

Gel Layer Permeability (GLP):

The permeability of a swollen gel layer under a confining pressure of 0.3 psi is determined as described in EP-A-0 640 330 as the gel layer permeability (GLP) of a swollen gel layer of superabsorbent polymer, although the apparatus described on page 19 and in FIG. 8 of the above-cited patent was modified to the effect that the glass frit (40) was no longer used, the piston (39) is made of the same plastic material as the cylinder (37) and now contains 21 equally sized holes uniformly distributed over the entire contact surface. The procedure and evaluation of the test method remains unchanged compared to the description in EP-A-0 640 330 and DE-A-195 43 366. The flow rate (g of NaCl solution/sec) is automatically recorded at certain time intervals.

GLP=($F_g(t=0)*L_0$)/($d*A*wP$)(cm$^3$*sec/g).

where ($F_g(t=0)$) is the flow rate of NaCl solution in g/sec obtained from a linear regression analysis of the $F_g(t)$ data of the flow rate conditions by extrapolation to t=0, $L_0$ is the thickness of the gel layer in cm, d is the density of the NaCl solution in g/cm$^3$, A is the area of the gel layer in cm$^2$ and WP is the hydrostatic pressure on the gel layer in dyn/cm$^2$.

INVENTIVE EXAMPLE 1

Under adiabatic conditions, a 2 l wide-neck cylindrical reaction flask is charged with 1080 g of completely ion-free water cooled to 15° C., and 430 g of acrylic acid and also 3.4 g of tetraallyloxyethane are dissolved therein. Nitrogen is passed into the monomer solution at a rate of about 2 l/min for about 20 min to lower the oxygen content. At an O$_2$ content of 1.5 ppm, 7.7 g of a 10% by weight aqueous solution of 2,2'-azobis(2-amidinopropane)dihydrochloride are added, followed, after passing in further N$_2$ and at an O$_2$ content of 1.3 ppm, by 2.6 g of a 1% by weight H$_2$O$_2$ solution and finally at an O$_2$ content of 1.0 ppm by the addition of 6.4 g of a 0.1% by weight ascorbic acid solution. The ensuing polymerization, in the course of which the temperature rises to about 75° C., produces a solid gel, which is subsequently subjected to mechanical comminution. 1000 g of the comminuted gel are admixed with 10 g of sodium silicate (27% by weight based on SiO$_2$ and 14% by weight based on NaOH), dissolved in 228.2 g of 50% by weight aqueous sodium hydroxide solution (degree of neutralization of the acrylic acid: 74 mol %), the gel thus obtained is passed twice through a mixing extruder, and the resultant gel particles are dried at above 150° C., ground and sieved.

The product obtained is characterized essentially, inter alia, by the following physical data, all measured in 0.9% by weight NaCl: extractables (1 h value) 2.1%, absorbency under load AUL (20 g/cm$^2$)=20.9 g/g, gel layer permeability (GLP)=3 ($\times 10^{-7}$ cm$^3$ sec/g).

100 g of the product thus obtained were sprayed with 10 g of a homogeneous solution consisting of 3.0 g of methanol, 7.0 g of water and 0.1 g of ethylene glycol diglycidyl ether in a powder mixing assembly and heat treated at 140° C. for 40 min.

The product obtained had the following performance data (measured in 0.9% aqueous NaCl solution):
Centrifuge retention: 33.1 g/g
AUL (60 g/cm$^2$): 24.7 g/g
GLP: 60 ($\times 10^{-7}$ cm$^3$ sec/g).

COMPARATIVE EXAMPLE 1

The polymerization is carried out completely analogously to Inventive Example 1, except that no sodium silicate solution is used in the workup to 1000 g of the comminuted gel, instead the neutralization is effected exclusively with 168 g of 50% by weight aqueous sodium hydroxide solution. The product obtained differs from the product of Inventive Example 1 in that it has no permeability whatever, i.e., does not allow any fluid to pass through the swollen gel layer and the GLP accordingly has a value of 0 ($10^{-7}$ cm$^3$ sec/g). On surface postcrosslinking this product similarly to Inventive Example 1, the postcrosslinked product merely has a gel layer permeability (GLP) of 20 ($10^{-7}$ cm$^3$ sec/g).

INVENTIVE EXAMPLE 2

A 10 l capacity polyethylene vessel thoroughly insulated by foamed plastic material is charged with 3500 g of completely ion-free water at 4° C. and 1800 g of acrylic acid are added with stirring. At this point 10.8 g of pentaerythritol triallyl ether are added and the solution is inertized by passing nitrogen into it. This is followed by the addition of the initiator system consisting of 2.5 g of 2,2'-azobisamidinopropane dihydrochloride (dissolved in 20 g of completely ion-free water), 4 g of potassium peroxodisulfate (dissolved in 50 g of completely ion-free water) and also 0.4 g of ascorbic acid (dissolved in 20 g of completely ion-free water), added in succession with stirring. The reaction solution is allowed to stand without stirring. The ensuing polymerization, in the course of which the temperature rises to about 90° C., produces a solid gel.

1000 g of the gel thus prepared are mechanically comminuted in the presence of a solution of 0.96 g of 27% sodium silicate (from MERCK) in 216.6 g of 50% NaOH and then treated once more in a mixing extruder. The resultant gel particles are dried at above 150° C. and ground.

100 g of the polymer powder thus prepared were sprayed with a solution of 7 ml of water, 3 g of methanol and 0.20 g of 2-oxazolidinone in a laboratory mixing assembly and heat treated at 175° C. for 60 min. The material obtained is characterized by the following product data:
Centrifuge retention: 24.6 g/g
AUL (60 g/cm$^2$): 23.9 g/g
GLP: 8 ($\times 10^{-7}$ cm$^3$ sec/g).

COMPARATIVE EXAMPLE 2

The polymerization is carried out completely analogously to Inventive Example 2, except that no sodium silicate solution is used in the workup to 1000 g of the comminuted gel, instead the neutralization is effected exclusively with 218.2 g of 50% by weight aqueous sodium hydroxide solution. The product obtained has, after surface postcrosslinking similarly to Inventive Example 2, a gel layer permeability of merely 4 ($\times 10^{-7}$ cm$^3$ sec/g).

INVENTIVE EXAMPLE 3

The polymerization is carried out completely analogously to Inventive Example 2, except that in the course of the workup 1000 g of the comminuted gel are neutralized with a solution of 4.9 g of 35% sodium silicate (27% of SiO$_2$+8% of Na$_2$O) in 215.2 g of 50% by weight NaOH and dried. 100 g of the polymer powder are sprayed with a solution of 0.01 g of sorbitan monococoate and 0.25 g of N-methyloxazolidinone in 10 ml of water in a laboratory mixing assembly and heat treated at 180° C. for 45 minutes. The product obtained is characterized by the following data:
Centrifuge retention CRC: 31.3 g/g
Absorbency under load, AUL 60 g/cm$^2$: 21.4 g/g
Gel layer permeability (GLP): 4 ($\times 10^{-7}$ cm$^3$ sec/g)

COMPARATIVE EXAMPLE 3

The polymerization is carried out completely analogously to Inventive Example 3, except that no sodium silicate solution is used in the workup to 1000 g of the comminuted gel, instead the neutralization is effected exclusively with 221.5 g of 50% by weight aqueous sodium hydroxide solution. The product obtained has, after surface postcrosslinking similarly to Inventive Example 3, the following data:
Centrifuge retention CRC: 31.8 g/g
Absorbency under load, AUL 60 g/cm$^2$: 20.9 g/g
Gel layer permeability (GLP): 1 ($\times 10^{-7}$ cm$^3$ sec/g)

COMPARATIVE EXAMPLE 4

Under adiabatic conditions, a 5 l wide-neck cylindrical reaction flask is charged with 2837 g of completely ion-free water cooled to 10° C., and 1040 g of acrylic acid and also 8.3 g of pentaerythritol triallyl ether are dissolved therein. Nitrogen is passed into the monomer solution at a rate of about 2 l/min for about 20 min to lower the oxygen content. At an O$_2$ content of 1.5 ppm, a solution of 0.52 g of 2,2'-azobis(2-amidinopropane)dihydrochloride in 25 g of completely ion-free water is added, followed, after passing in further N$_2$ and at an O$_2$ content of 1.3 ppm, by 12.165 g of a 0.47% H$_2$O$_2$ solution and finally at an O$_2$ content of 1.0 ppm by 16.5 g of a 0.1% by weight ascorbic acid solution. The ensuing polymerization, in the course of which the temperature rises to about 75° C., produces a solid gel, which is subsequently subjected to mechanical comminution. 1000 g of the comminuted gel are admixed with 216.7 g of 50% by weight aqueous sodium hydroxide solution (degree of neutralization of the acrylic acid: 74 mol %), the gel thus obtained is passed twice through a mixing extruder and the resultant gel particles are dried at above 150° C., ground and sieved.

The product obtained is characterized essentially, inter alia, by the following physical data, all measured in 0.9% by weight NaCl:
Extractables (1 h value): 3.7%,
Absorbency under load (AUL, 21 g/cm$^2$): 11.1 g/g,
Centrifuge retention (CRC): 33.8 g/g,
Gel layer permeability (GLP): 0.1 ($10^{-7}$ cm$^3$ sec/g).

Similarly, 1000 g lots of the polyacrylate gel prepared according to Comparative Example 4 were then utilized with varying mixture amounts of sodium silicate/50% NaOH or sodium silicate/alkali metal carbonate. In each case sodium silicate from MERCK was used, containing 27% by weight of $SiO_2$ and 8% by weight of $Na_2O$.

Use levels and product data of Preparation Examples 4 to 9 are reported below in Table 1:

TABLE 1

| Example | Sodium silicate (for 1000 g of gel) g | Alkali (for 1000 g of gel) | pH | CRC g/g | AUL (21 g/ $cm^2$) g/g | GLP $10^{-7}$ $cm^3$ sec/g |
|---|---|---|---|---|---|---|
| Comp. 4 | — | 216.7 g NaOH 50% | 5.83 | 33.8 | 11.1 | 0.1 |
| Inv. 4 | 288.9 | 124.2 g NaOH 50% | 5.65 | 17.9 | 20.5 | 10 |
| Inv. 5 | 288.9 | 110.0 g $K_2CO_3$ | 5.66 | 17.1 | 19.9 | 8 |
| Inv. 6 | 288.9 | 85.0 g $Na_2CO_3$ | 5.63 | 18.0 | 20.1 | 11 |
| Inv. 7 | 481.5 | 62.6 g NaOH 50% | 5.49 | 15.0 | 17.3 | 32 |
| Inv. 8 | 481.5 | 124.2 g NaOH 50% | 7.48 | 15.4 | 16.9 | 28 |
| Inv. 9 | 674.0 | 1.0 g NaOH 50% | 5.20 | 11.9 | 14.8 | 45 |

COMPARATIVE EXAMPLE 4A 100 g of the product obtained according to Comparative Example 4 were sprayed with 10.42 g of a homogeneous solution consisting of 6.0 g of 1,2-propanediol, 2.3 g of water, 2.0 g of a polyamidoamine resin in 15% aqueous solution (RESAMIN® VHW 3608 from Clariant GmbH) and 0.12 g of $Al_2(SO_4)_3 \cdot 18H_2O$ in a powder mixing assembly and heat treated at 140° C. for 120 min.

The product obtained had the following performance data (measured in 0.9% by weight aqueous NaCl solution):
Centrifuge retention: 28.2 g/g
AUL (60 g/$cm^2$): 24.6 g/g
GLP: 20 ($10^{-7}$ $cm^3$ sec/g).

Further polyacrylate gels prepared according to Comparative Example 4 and neutralized with varying mixture amounts of sodium silicate/50% NaOH were surface postcrosslinked similarly to Comparative Example 4a.

Use levels and product data of Preparation Examples 10 to 15 are reported below in Table 2:

TABLE 2

| Example | Sodium silicate (for 1000 g of gel) g | 50% NaOH (for 1000 g of gel) g | CRC g/g | AUL (60 g/ $cm^2$) g/g | GLP $10^{-7}$ $cm^3$ sec/g |
|---|---|---|---|---|---|
| Comp. 4a | — | 216.7 | 28.2 | 24.6 | 20 |
| Inv. 10 | 9.6 | 213.6 | 27.2 | 24.0 | 35 |
| Inv. 11 | 19.3 | 210.5 | 26.7 | 23.3 | 41 |
| Inv. 12 | 28.9 | 207.4 | 24.7 | 23.2 | 52 |
| Inv. 13 | 38.5 | 204.3 | 24.3 | 22.9 | 65 |
| Inv. 14 | 48.1 | 201.3 | 24.2 | 22.7 | 75 |
| Inv. 15 | 96.3 | 155.1 | 22.7 | 21.4 | 87 |

COMPARATIVE EXAMPLE 16

A 10 l capacity polyethylene vessel thoroughly insulated by foamed plastic material is charged with 3650 g of completely ion-free water at 20° C. and 500 g of sodium bicarbonate are suspended therein. 2000 g of acrylic acid are metered into the stirred suspension at such a rate that excessive foaming due to ensuing $CO_2$ evolution is avoided. In the course of the addition, the monomer solution cools down to about 13° C. This is followed by the addition of 3 g of sorbitan monococoate (dispersed in 100 g of completely ion-free water) and also 8.1 g of allyl methacrylate and inertization of the solution by passing nitrogen into it. This is followed by the successive addition with stirring of the initiator system consisting of 1.66 g of 2,2'-azobisamidinopropane dihydrochloride (dissolved in 20 g of completely ion-free water), 3.3 g of potassium peroxodisulfate (dissolved in 150 g of completely ion-free water) and also 0.3 g of ascorbic acid (dissolved in 25 g of completely ion-free water). The reaction solution is allowed to stand without stirring. The ensuing polymerization, in the course of which the temperature rises to about 110° C., produces a solid gel.

1000 g lots of the gel thus prepared are mechanically comminuted in the presence of a solution containing different amounts of 27% sodium silicate (from MERCK) in 50% NaOH and then treated once more in a mixing extruder. The resultant gel particles are dried in a hot air stream at 170° C. and then ground and sieved.

Use levels and product data of Preparation Examples 16 to 19 are reported below in Table 3:

TABLE 3

| Example | Sodium silicate (for 1000 g of gel) g | 50% NaOH (for 1000 g of gel) g | pH | CRC g/g | AUL (35 g/ $cm^2$) g/g | GLP $10^{-7}$ $cm^3$ sec/g |
|---|---|---|---|---|---|---|
| Comp. 16 | — | 18.35 | 4.4 | 20.7 | 10.8 | 2.5 |
| Inv. 17 | 30.8 | — | 4.3 | 17.2 | 15.4 | 14 |
| Inv. 18 | 61.7 | — | 4.3 | 17.7 | 15.3 | 23 |
| Inv. 19 | 123.3 | — | 4.5 | 18.7 | 15.6 | 27 |

COMPARATIVE EXAMPLE 20

Under adiabatic conditions, a 5 l wide-neck cylindrical reaction flask is charged with 2942 g of completely ion-free water cooled to 10° C., and 1000 g of acrylic acid and also 4.5 g of pentaerythritol triallyl ether are dissolved therein. Nitrogen is passed into the monomer solution at a rate of about 2 l/min for about 20 min to lower the oxygen content. At an $O_2$ content of 1.5 ppm, a solution of 0.52 g of 2,2'-azobis(2-amidinopropane)dihydrochloride in 25 g of completely ion-free water is added, followed, after passing in further $N_2$ and at an $O_2$ content of 1.3 ppm, by 12 g of a 0.47% $H_2O_2$ solution and finally at an $O_2$ content of 1.0 ppm by 16.5 g of a 0.1% by weight ascorbic acid solution. The ensuing polymerization, in the course of which the temperature rises to about 70° C., produces a solid gel, which is subsequently subjected to mechanical comminution.

1000 g lots of the gel thus prepared are mechanically comminuted and neutralized with NaOH (Example 20) or with 27% sodium silicate (from MERCK) (Examples 21-24) and subsequently treated once more in a mixing extruder. The resultant gel particles are dried in a hot air stream at 100° C. and then ground and sieved.

Use levels and product data of Preparation Examples 20 to 24 are reported below in Table 4:

TABLE 4

| Example | Sodium silicate (for 1000 g of gel) g | 50% NaOH (for 1000 g of gel) g | pH | CRC g/g | GLP $10^{-7}$ cm$^3$sec/g |
|---|---|---|---|---|---|
| Comp. 20 | — | 75 | 4.36 | 29.5 | 1 |
| Inv. 21 | 244 | — | 4.03 | 15.3 | 12 |
| Inv. 22 | 305 | — | 4.25 | 18.9 | 17 |
| Inv. 23 | 350 | — | 4.36 | 19.7 | 21 |
| Inv. 24 | 400 | — | 4.50 | 20.6 | 25 |

INVENTIVE EXAMPLE 25

Under adiabatic conditions, a 5 l wide-neck cylindrical reaction flask is charged with 2840 g of completely ion-free water cooled to 10° C. 77.0 g of 35% sodium silicate from MERCK (27% by weight of SiO$_2$+8% by weight of Na$_2$O) and 1040 g of acrylic acid and also 10.4 g of pentaerythritol triallyl ether are dissolved in the initial charge. Silicate and acrylic acid have to be added slowly and in the correct order to avoid precipitating the sodium silicate. Nitrogen is passed into the monomer solution at a rate of about 2 l/min for about 20 min to lower the oxygen content. At an O$_2$ content of 1.5 ppm, a solution of 0.52 g of 2,2'-azobis(2-amidinopropane) dihydrochloride in 25 g of completely ion-free water is added, followed after the passing in of further N$_2$ at an O$_2$ content of 1.3 ppm by 12.165 g of a 0.47% H$_2$O$_2$ solution and finally at an O$_2$ content of 1.0 ppm by 16.0 g of a 0.1% ascorbic acid solution. The ensuing polymerization, in the course of which the temperature rises to about 75° C., produces a solid gel, which is subsequently subjected to mechanical comminution. 1000 g of the comminuted gel are admixed with 198 g of 50% by weight aqueous sodium hydroxide solution, and passed twice through a mixing extruder, and the resultant gel particles are roll dried at a dryer surface temperature of about 180° C., ground and sieved.

The product obtained is characterized essentially, inter alia, by the following physical data (all measured in 0.9% NaCl):
Absorbency under load (AUL, 21 g/cm$^2$): 21.6 g/g,
Centrifuge retention (CRC): 30.0 g/g.

100 g of the product obtained were sprayed with 10.00 g of a homogeneous solution consisting of 3.83 g of 1,2-propanediol, 4.05 g of water, 2.0 g of a polyamidoamine resin in 15% aqueous solution (RESAMIN VHW 3608® from CLARIANT GmbH) and 0.12 g of Al$_2$(SO$_4$)$_3$.18H$_2$O in a powder mixing assembly and heat-treated at 140° C. for 120 min.

The product obtained was characterized by the following physical data (all measured in 0.9% NaCl):
Centrifuge retention: 26 g/g
AUL (60 g/cm$^2$): 24 g/g
GLP: 62 ($10^{-7}$ cm$^3$ sec/g).

COMPARATIVE EXAMPLE 25

The polymerization is carried out completely analogously to Inventive Example 25, except that no sodium silicate is used and instead 214 g of 50% by weight NaOH are used for 1000 g of polymer gel in the subsequent neutralization. Drying and grinding are likewise identical to Inventive Example 25.

The product obtained is characterized essentially, inter alia, by the following physical data (all measured in 0.9% NaCl):
Absorbency under load (AUL, 21 g/cm$^2$): 12.0 g/g
Centrifuge retention (CRC): 32.8 g/g.

100 g of the product obtained were surface postcrosslinked likewise completely analogously to Inventive Example 25 to obtain a product characterized by the following physical data (all measured in 0.9% NaCl):
Centrifuge retention: 28 g/g
AUL (60 g/cm$^2$): 24 g/g
GLP: 33 ($10^{-7}$ cm$^3$ sec/g).

We claim:

1. A process for preparing dried hydrogel particles, comprising:
   polymerizing an olefinically unsaturated carboxylic acid or its salts in a polymerization reaction mixture, to obtain a solid gel containing a polymer;
   admixing the polymerization reaction mixture before or during the polymerization or admixing said solid gel with an alkali metal silicate of the general formula I $$M_2O \cdot nSiO_2 \quad \text{(I)},$$

wherein M is an alkali metal and n is from 0.5 to 4;
   thereby obtaining particles of a gel in which said silicate is evenly distributed;
   postcrosslinking said particles of the gel; and
   drying said particles of the gel at an elevated temperature, to obtain said dried hydrogel particles;
   wherein said postcrosslinking is effected by a crosslinker which is a compound containing two or more groups that form covalent bonds with the carboxyl groups of said particles of the gel;
   wherein said polymer is prepared by admixing said alkali metal silicate in an amount of from 0.05% by weight to 20% by weight, reckoned on SiO$_2$ and based on a total monomer weight.

2. A dried hydrogel, prepared by
   polymerizing an olefinically unsaturated carboxylic acid or its salts in a polymerization reaction mixture;
   admixing the polymerization reaction mixture, before or during the polymerization and before drying, with an alkali metal silicate of the general formula I $$M_2O \cdot nSiO_2 \quad \text{(I)},$$

wherein M is an alkali metal and n is from 0.5 to 4;
   postcrosslinking a resulting polymer in which said silicate is evenly distributed;
   thereby obtaining a hydrogel containing said postcrosslinked polymer; and
   drying said hydrogel at an elevated temperature, to obtain said dried hydrogel;
   wherein said postcrosslinking is effected by a crosslinker which is a compound containing two or more groups that form covalent bonds with the carboxyl groups of said polymer;
   wherein said polymer is prepared by admixing said alkali metal silicate in an amount of from 0.05% by weight to 20% by weight, reckoned on SiO$_2$ and based on a total monomer weight.

3. The dried hydrogel according to claim 2 which is capable of absorbing an aqueous fluid.

4. The dried hydrogel according to claim 2, wherein M in formula (I) is sodium.

5. The dried hydrogel according to claim 2, wherein M in formula (I) is potassium.

6. The dried hydrogel according to claim 2, wherein said polymer is water-insoluble.

7. The dried hydrogel according to claim 2, wherein said polymer is a copolymer.

8. The dried hydrogel according to claim 2, wherein said alkali metal silicate is soluble in water.

9. The dried hydrogel according to claim 2, wherein said olefinically unsaturated carboxylic acid is selected from the group consisting of acrylic acid, methacrylic acid, crotonic acid, 2-acryl-amido-2-methylpropanesulfonic acid, 2-acryl-amido-2-methylpropanephosphonic acid, vinylphosphonic acid and mixtures thereof.

10. A method for absorbing aqueous solutions, dispersions and emulsions, comprising:
contacting the dried hydrogel according to claim 2 with an aqueous solution, dispersion or emulsion.

11. A process for preparing dried hydrogel particles, comprising:
polymerizing an olefinically unsaturated carboxylic acid or its salts in a polymerization reaction mixture, to obtain a solid gel containing a polymer;
admixing the polymerization reaction mixture before or during the polymerization with an alkali metal silicate of the general formula I $$M_2O \times nSiO_2 \qquad (I),$$

wherein M is an alkali metal and n is from 0.5 to 4;
thereby obtaining particles of a gel in which said silicate is evenly distributed;
postcrosslinking said particles of the gel; and
drying said particles of the gel at an elevated temperature, to obtain said dried hydrogel particles;
wherein said postcrosslinking is effected by a crosslinker which is a compound containing two or more groups that form covalent bonds with the carboxyl groups of said particles of the gel;
wherein said polymer is prepared by admixing said alkali metal silicate in an amount of from 0.05% by weight to 20% by weight, reckoned on $SiO_2$ and based on a total monomer weight.

12. The process as claimed in claim 11, wherein said polymerization is performed in a homogeneous phase.

13. The process as claimed in claim 11, wherein said admixing of the polymerization reaction mixture with an alkali metal silicate of the general formula I is before the polymerization and before drying.

14. The process as claimed in claim 11, wherein said admixing of the polymerization reaction mixture with an alkali metal silicate of the general formula I is during the polymerization and before drying.

15. The process as claimed in claim 11, wherein said postcrosslinking is effected using a crosslinker selected from the group consisting of polyglycidyl ethers, haloepoxy compounds, polyols, polyamines, polyisocyanates, polyfunctional aziridine compounds, alkyl di(tri)halides and oil-soluble polyepoxy compounds.

16. The process as claimed in claim 11, wherein the alkali metal silicate of the formula I is in the form of an aqueous solution.

17. The process as claimed in claim 11, wherein, at a polymer pH of from 5.0 to 9.0, the gel permeability is at least $25 \times 10^{-7}$ cm$^3$ sec/g, and
wherein at a polymer pH of less than 5.0, the gel permeability is in particular at least $4 \times 10^{-7}$ cm$^3$ sec/g.

18. The process as claimed in claim 11 wherein said postcrosslinking is performed with mono-, bis- and polyoxazolidinones, or with the cyclic ester of propanediol with silicic acid of the formula II

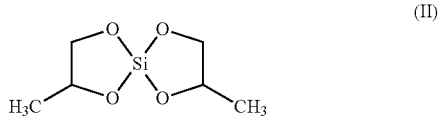

or with di-, tri- or polyepoxides, haloepoxy compounds, polyamine compounds or polyhydric alcohols.

* * * * *